United States Patent [19]

Hamada

[11] Patent Number: 5,250,305

[45] Date of Patent: Oct. 5, 1993

[54] PROCESS FOR ENZYMATIC ULTRAFILTRATION OF DEAMIDATED PROTEIN

[75] Inventor: Jamel S. Hamada, Metairie, La.

[73] Assignee: The United States of America as represented by the Secretary of Agriculture, Washington, D.C.

[21] Appl. No.: 544,562

[22] Filed: Jun. 27, 1990

Related U.S. Application Data

[63] Continuation-in-part of Ser. No. 369,587, Jun. 21, 1989, Pat. No. 5,082,672.

[51] Int. Cl.$^5$ .............................. A23J 1/14; A23J 3/16
[52] U.S. Cl. ............................... 426/46; 426/52; 426/656; 426/478; 426/490; 426/495
[58] Field of Search ................. 426/7, 40, 42, 46, 52, 426/63, 656, 478, 490, 495, 44, 49

[56] References Cited

U.S. PATENT DOCUMENTS 4,302,473 11/1981 Mikami et al. .................. 426/46
4,757,007 7/1988 Satoh et al. .................... 426/46

FOREIGN PATENT DOCUMENTS 0201247 7/1983 Fed. Rep. of Germany ........ 426/46
49-25346 6/1974 Japan ................................. 426/46

OTHER PUBLICATIONS

Hamada 1989 Preparation and Functional Protein of Enzymatically Deamidated Soy Proteins, J. Food Science 54(3) 598.
Hamada et al. J. Food Science, vol. 53, No. 2, (1988) pp. 671-672, [7683].
Hamada et al. J. Food Science, vol. 53, No. 4, (1988), pp. 1132-1149 [7728].

*Primary Examiner*—Carolyn Paden
*Attorney, Agent, or Firm*—M. Howard Silverstein; John D. Fado; Joseph A. Lipovsky

[57] ABSTRACT

This invention relates to methods for the large-scale enzymatic deamidation of foot proteins. Deamidating enzymes such as peptidoglutaminase are immobilized using a spiral membrane having a molecular weight cut-off, from about 3 to about 50 kd. The methods minimize loss of the enzymatic activity for subsequent reuse of the enzyme as well as increase deamidation product yield.

9 Claims, 7 Drawing Sheets

Concentration

Diafiltration

Recycling

Diafiltration

PROCESS FOR ENZYMATIC ULTRAFILTRATION OF DEAMIDATED PROTEIN

CROSS REFERENCE TO RELATED APPLICATION

This is a continuation-in-part of copending U.S. Ser. No. 07/369,587, filed Jun. 21, 1989 which is now U.S. Pat. No. 5,082,672.

BACKGROUND OF THE INVENTION

1. Field of the Invention

This invention relates to methods for the large-scale enzymatic deamidation of foot proteins. The deamidation proteins have utility as emulsifying or foaming agents in many food systems.

2. Description of the Prior Art

The functional properties of foot proteins depend on their conformation in food systems. The relationship of protein structure to functionality is such that altering the chemistry of food proteins can improve functional properties such as solubility, viscosity, gelation, fat emulsification and foaming. The conversion of protein amide groups of carboxyl groups by deamidation improves solubility and other physical properties of protein under mildly acidic conditions.

Improving solubility, emulsifying or foaming properties of edible proteins enchance their use as functional ingredients in many food systems, including beverages, pourable and nonpourable dressings, whipped toppings, frozen desserts, confections, baked goods and meat.

An enzymatic aproach to protein deamidation offers serval advantages over a chemical approach, including the speed of reaction, the fact that the reactions take place under mild conditions such as neutral pH and room temperature and most importantly, they are highly specific. The mild conditions reduce energy costs and the high specificity increases processing efficiency and minimize the need for downstream processing.

Hamada et al., (*J. Food Sci.* 53:1132; 1988) used the peptidoglutaminase from *B. circulans* todeamidation soy peptides and proteins. Peptidoglutaminase (PGase) readily deamidation soypeptides but its activity towards the intaaaact protein was small. They suggest that limited deamidation was due to the large molecular size and/or unique conformation of soy protein. There is a need to provide for an efficient enzymatic deamidation process for food proteins of large molecular size and unique conformation at near physiological pH.

Enzyme immobilization provides effective utilization and useful saving of enzyme in food processing. However, there are several disadvantages using immobilization techniques, including material cost, binding efficiency and the selection of an appropriate support. These drawbacks have made the technique difficult to apply commercially. Several investigators have employed ultrafiltration (UF) in enzyme immobilization and enzyme recovery for recycling processes. In comparison to coinventional immobilization techniques, UF methods can be simpler, less expensive and a more efficient. Additionally, using UF may improve yield, production consistency and product quality.

UF is used in the dairy industry for concentrating protein components in milk, for cheese manufacturing and for preparation of whey protein concentrates. Additionally, it has been used experimentally for separation of lysozyme egg white; clarification of juice; and removal of bacteria, viruses, and other organisms in the production of sterile products (Modler et al., *Food Technol.* 42(10):114; 1987).

PGase produced by *Bacillus circulans* has recently been used in the deamidation of casein and whey protein hydrolysates (Gill et al., *Irish J. Food Sci. Tech.* 9:30; 1985) and soy peptides and proteins (Hamada et al., *J. Food Sci.* 53:671 1988). Enzymatic deamidation of food proteins improves solubility and other functional properties of proteins under mildly acidic conditions (Hamada and Marshall, *J. Food Sci.* 54:598 1989; Kato et al., *J. Food Sci.* 54:1345 1989).

In rendering large molecular weight protein substrates for PGase deamidation, reducing protein size is an inevitable step in the process. Hamada and Marshall (1988) reported a quantitative relationship between the extent of deamidation and the degree of protein hydrolysis combined with heat treatment. Proteolysis provides polypeptides with different molecular sizes and many times smaller than the large molecular weight (MW) PGase. Kikuchi and Sakaguchi (*Agri. Biol. Chem.* 37:827; 1973) reported that the MW of PGase I and II, estimated by gel filtration to be 200 kd for both in a non-dissociating salt and pH consitions.

UF reactors are well-mixed reactors. Blatt et al., (*Anal. Biochem.* 26:151; 1968) reported the possibility of using ultrafiltration membranes to separate higher molecular weight biologically active substances from lower molecular weight solutes. Because of the selective nature of the UF membrane this type of reactor is most useful for carrying out enzyme reactions using membranes that are impermeable to the enzyme, but permeable to substrates and products. UF immobilization of enzymes offer several distinct advantages relative to other immobilization methods. Immobilization is achieved without chemical alternation of the enzyme and can be accomplished quickly and easily (Chambers et al., *Meth. Enzymol.* 44:291; 1976).

Butterworth et al (*Biotechol. Bioeng.* 12:615; 1970) were the first to use UF concept to immobilize alpha-amylase in a continuous reactor to hydrolyze starch. Abbott et al. (*Biotechnol. Bioeng.* 18:1033; 1976) reported a successful use of cephalosporin acetylesterase in an UF reactor.

Desselie and Cheryan (*J. Food Sci.* 46:1035; 1981) developed a continuous method for the enzymatic proteolysis of proteins in an UF reactor. There are major disadvantages using separated or immobilized biocatalysts such as enzymes. Losses in enzyme activity of 10–90% have been reported (Cheetham, "Handbook of Enzyme Biotechnology," A Wiseman (Ed.) Ellis Horwood Limited Publishers, Chichester and New York, p. 54; 1986). Additionally, product recovery has traditionally been low because of concentration polarization and membrane fouling.

SUMMARY OF THE INVENTION

It is therefor and object of the present invention to provide methods for the enzymatic ultrafiltration deamidation of food proteins that does not suffer disadvantages of the prior art such as loss of enzyme activity and low product yield. Accordingly, a UF membrane with a suitable pore size, e.s. of up to a 100 kd membrane, are impermeable to undissociated units of PGase but permeable to food proteins and their deamidated products is incorporated into a UF reactor. Solubilized food proteins and PGase are added resulting in almost complete deamidation with essentially no lose in enzyme activity. Thus, employing UF in PGase recovery for recycling, i.e. physical immobilization, allows for the production of enzymatically deamidated food proteins with enhanced solubility and functional properties.

Additionally, it is another object of the present invention to provide a batch UF reactor developed for the large-scale enzymatic deamidation of food protein.

Currently, the addition of enzymes to food products requires the Food and Drug Administrations approval. Therefore, in the context of the present invention, deamidating enzymes are advantageously kept separate from the final product and thus are not considered food additive.

Figure 6:
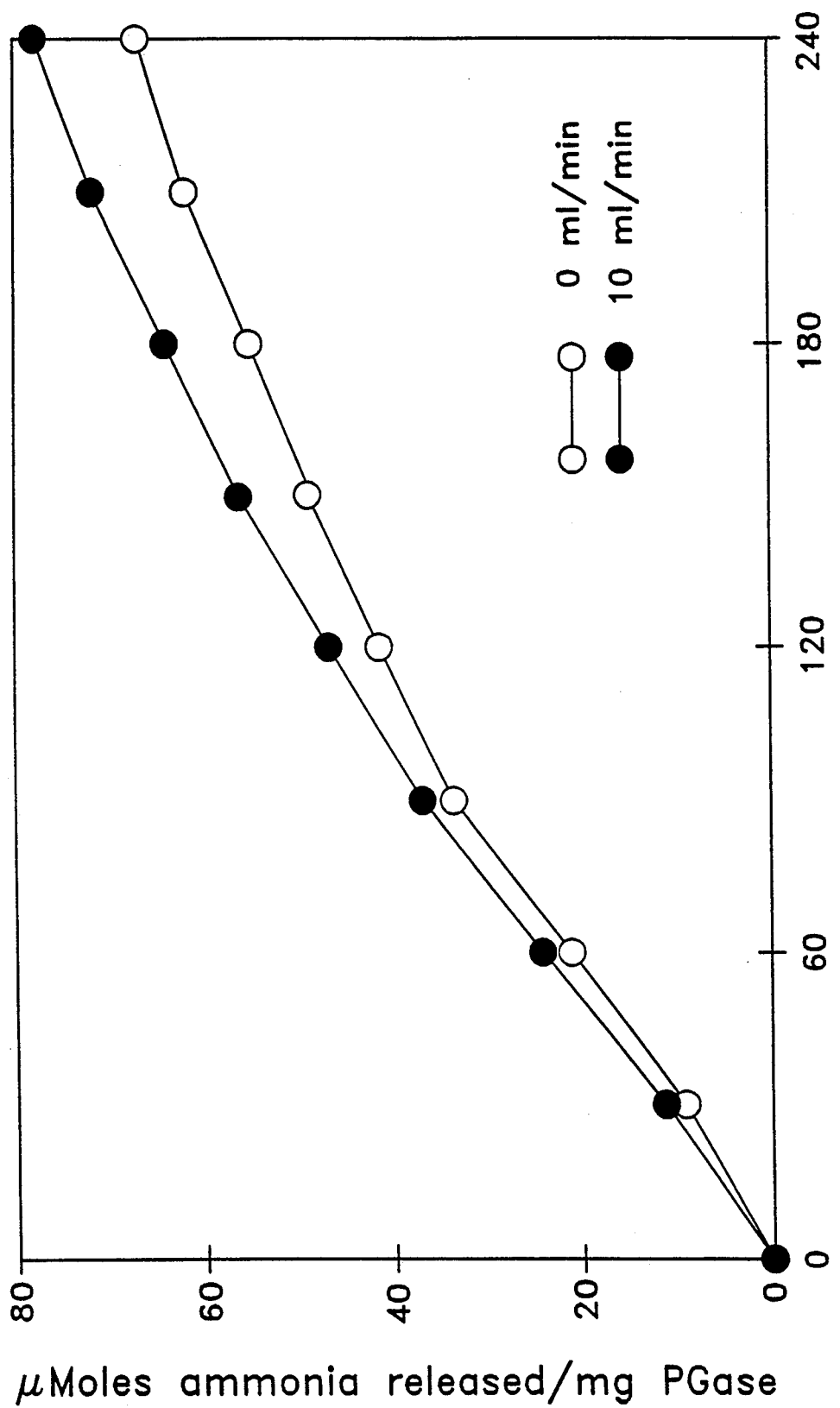

A (O) Calculated from Michaelis-Menten equation,
B (●) Predicted from Michaelis-Menten equation for mixed zero and first order kinetics,
C (Δ) Measured experimentally FIG. 6 Effect of ultrafiltration (UF) in recycling mode on PGase activity toward Peptone IV: (O) No UF; (●) Recycling at 10 ml/min.

Figure 7:
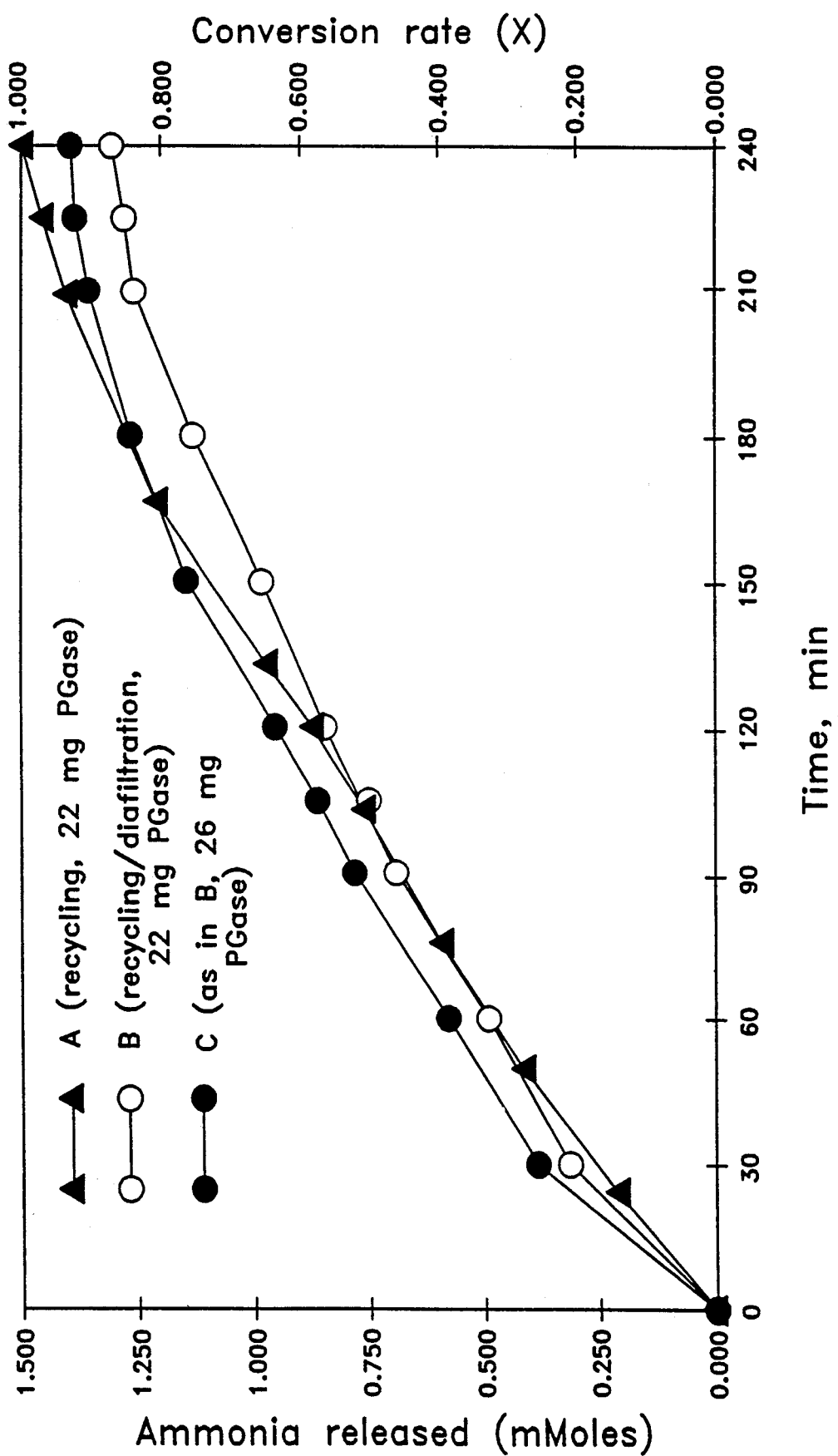

FIG. 7 Progress curves for Peptone IV deamination by immobilized PGase in recycling mode (RM) and diafiltration mode (DM):

A (▲) RM, Eo=22 mg
B (O) RM for 120 min, DM for 120 min, Eo=2 mg
C (●) RM for 105 min, DM for 135 min, Eo=26 mg

DESCRIPTION OF THE TERMINOLOGY

Nomenclature $E_o$ the enzyme quantity (in mg) present at zero time.
$V_{max} = EK_2$ is the product of the enzyme present and its activity (v).

$n_o$ the operational effectiveness factor is the activity of the immobilized enzyme divided by the activity of free enzyme. Where an effectiveness value of 1.0 is obtained, this indicates that the activity if the enzyme has not been reduced appreciably by immobilization, mass transfer, or diffusional restrictions.

$K_o$ Michaelis-Menten constant, expressed in micromoles/mL $S_o$ the initial substrate concentration (micromoles/mL)

t time of reaction (min).

v the initial rate of enzyme catalyzed reaction (micromoles/min/mg or micromoles/min/mL).

V the total volume of reaction mixture (mL) including the fluid in any circulation tube or the membrane itself.

$V_{max}$ maximum velocity of enzyme catalyzed reaction, expressed in micromoles/min/mL.

X conversion rate.

$$X = \frac{(S_o - S)}{SO}$$

Where $S_o$ and $S$ are substrate concentration at O time and at t time.

GLOSSARY

Concentration: Retentate is circulated back to feed solution so that the retained components are usually more concentrated than they were in the original feed solution.

Diafiltration: The exchange of process solution with fresh buffer solution (or other solvent), thus removing the membrane permeating species from the batch. In continuous diafiltration solvent is added continuously to the feed reservoir (or tank) at the same rate as permeate flux. Discontinuous diafiltration is a mode of ultrafiltration processing where solvent is added to the concentrated retentate to dilute it back to a certain volume.

Flux: Flow rate or the rate at which fluid passing through the membrane, usually expressed in volume per membrane area per unit time.

MWCO: Molecular weight cut-off, describing the nominal rejection of a known feed solute, i.e. the effectiveness of membrane in retaining or allowing passing of solute species.

Permeate: Portion of the feed solution which passes through the membrane.

Recycle: An UF mode in which both retentate and permeate return back to the feed tank.

Retentate: The portion of the feed solution which does not pass through the membrane and contains retained solutes at a concentration higher than that of the original feed solution.

Ultrafiltration (UF): UF is a membrane separation process in which applied hydraulic pressure forces solvent and solvents and solutes in the feed solution whose molecular weights are below the membrane MWCO through the membrane and emerge as permeate, while rejected species, or retentate, are concentration in the feed solution.

DETAILED DESCRIPTION OF THE INVENTION

The subject of the present invention is related to the copending U.S. patent application Ser. No. 07/369,587 entitled, "Enzymatic Deamidation of Food Proteins," the disclosure of which is incorporated by reference. Ultrafiltration (UF) of *Bacillus circulans* cell extract using a membrane with molecular weight cut-off (MWCO) of 30 kd increased the specific activity of peptidoglutaminase (PGase) in the retentate only slightly, but there was no activity detected in the permeate. Retentate was used to sequentially deamidate 4 batches of a soy protein hydrolysate at an initial enzyme-to-substrate rate sufficient for the complete deamidation of the peptone in 2 hr at 30° C.

UF using a spiral wound membrane with MWCO of 30 kd. About 100% conversion of the glutamine amides in the peptone was obtained in every run and 96.7% of PGase was recovered after the 4th run. No inactivation or leakout occurred during each run. UF is a suitable technique for immobilization of PGase by containment within a 30 kd membrane in the design of a batch or continuous reactor for the deamidation of food proteins or protein hydrolysates.

A batch UF reactor was developed for large-scale enzymatic deamidation of food proteins in order to improve their functional properties. A soy protein hydrolysate, used as a model, was deamidated with PGase immobilized by containment within an UF device employing a 30 kd spiral membrane.

The 1L reactor was operated at 30° C. and 10mL/min flux in recycling mode until 60% of substrate was converted to products then in diafiltration mode for 120 min. A Michaelis-Menten equation integrated for mixed zero and first-order kinetics was used to predict the enzyme performance in order to optimize the deamidation reaction of the soy peptone. The predicted time course closely matched the time course measures experimentally. Effectiveness factor was incorporated in the equation to take care of the interaction of kinetics with the effects of UF on progress of deamidation. The minimum enzyme dosage (26 mg) required for the complete deamidation of 1.5 millimoles amides at the end of UF run was accurately calculated using the equation. At the end of batch run about 96% of the glutamine amides were converted and 99% of enzyme recovery was obtained.

EXAMPLE 1

Secton I: Potential of Ultrafiltration for Physical Immobilization of Peptidoglutaminase

MATERIALS AND METHODS

Materials

*Bacillus circulans* culture (ATCC #21590) was obtained from the American Type Culture Collection, Rockville, Md. Peptone type IV and CBZ-L-glutamine was purchased from Sigma Chemical Co., St. Louis, Mo. and t-BOC-L-glutaminyl-L-proline from Peptides International, Louisville, Ky. The BCA (bicinchoninic acid) protein assay reagent was from Pierce Chemical Co. (Rockford, Ill.). Other chemicals were reagent grade or the highest purity obtainable.

Preparation and assay of PGase

*B. circulans* cells were grown and harvested then PGase was extracted with 0.01 M phosphate buffer, ph 8.0, as previously reported (Hamada et al., 1988). The cell extract of *B. circulans* and its UF fractions, were evaluated for PGase I and II activities using the synthetic substrates CBZ-L-glutamine and t-BOC-L-glutaminyl-L-proline, respectively. The deamidating ability of PGase preparations toward soy protein hydrolysates was assessed using peptone type IV as substrate. Peptone type IV is an enzymatically hydrolyzed soy protein with approximately 23% of the peptide bonds cleaved (i.e. 23% DH), according to Sigma Chemical Do. To 5 mL substrate containing 25–50 moles amides in 0.05 M phosphate buffer, pH 7.0, 1 mL enzyme preparation containing 0.25–0.50 mg protein was added and the reaction mixtures were incubated at 30° C. for 2 hrs. Then the ammonia content of the samples was determined with a model 95-10 ammonia electrode (Orion Research Inc., Cambridge, Mass.). One unit of enzyme activity (mg enzyme protein) frees one micromole of ammonia from the substrate after 2 hr incubation at 30° C.

PGase Purification by Ultrafiltration

A hollow fibers (H1P 100-43), with molecular weight cut off (MWCO) of 100 kd, and a Spiral wound S1-Y30 membrane with MWCO of 30 kd, both from Amicon Corp (Amicon Corp., Lexington, Mass.), were used to purify 400 mL of cell extract containing 0.05–0.10% protein. Membranes were mounted to a CH2 Amicon system. The 100 kd membrane was first coated with ovalbumin prior to use. The spiral membrane, purchased while UF experiments were in progress, did not need coating, according to the manufacturer, Amicon Corp.

Figure 1A:
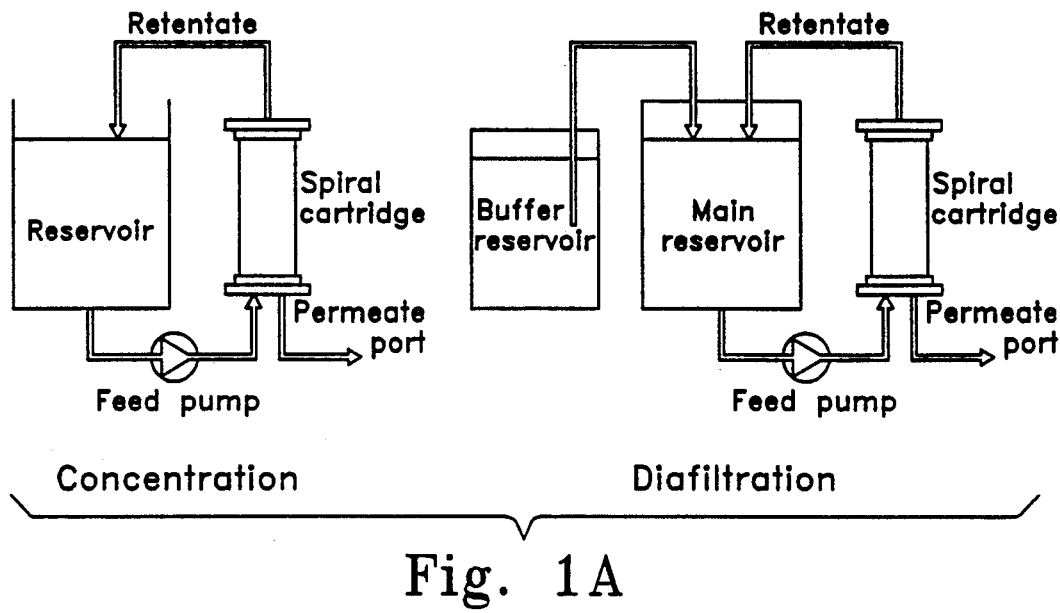
FIG. 1 Schematic diagram of the operational modes of (A) UF device and (B) UF reactor system.

The UF unit was run at 5° C in a diafiltration mode, in which the ultrafiltration was replaced by the continuous addition of 0.01 M phosphate buffer, 7.0, from a separate reservoir (FIG. 1A), for 2 hrs at an average flow rate of 10.0 mL/min. Specific activities of the retentate and permeate fractions, toward the synthetic substrates CBZ-Gln and BOC-Gln-Pro as well as peptone type IV, were measured.

UF Recovery for Multiple Reuse of PGase

The 100 or 30 kd membrane was used to filter about 1500 mL 5% peptone solution prior to its use in deamidation. About 750 mL 1% peptone solution, in 0.905 M phosphate buffer, pH 7.0 were deamidation by incubation with 60 mg retentate PGase for 2 hr at 30° C. These amounts of enzyme were corresponding to initial E/S ratio that was 1.5 times higher than that required for the completion of peptone deamidation. The enzyme was then removed from the deamidation peptone by UF (FIG. 1A) using 100 kd or 30 kd membrane at 10 mL/min in diafiltration mode for 1 hr and concentration mode for another hour at 25° C. At the end of each process, about 1.2 L of deamidated peptone and 150–200 mL retentate were obtained. This process of deamidation and UF separation of PGase was sequentially repeated 3 more times with volume and peptone quantities adjusted for residual enzyme after sampling. Specific activities of retentate and permeate were determined before and after each run. The extent of peptone deamidation was determined by measuring the ammonia released enzymatically in the permeated peptone after each run.

Chemical Analysis

Protein content for the soy protein hydrolysate was measured by the Kjeldahl method and for PGase by the BCA method of Smith et al. (*Anal. Biochem.* 150:76; 1985). The amide content of protein was measured according to Wilcox (*Meth. Enzymol.* 11:63; 1967).

Partial Purification of PGase using a 100 kd Membrane

Ultrafiltration, using a membrane with a MWCO of 100,000 increased the specific activity of cell extract, retained by the membrane, 1.5 fold, but had no effect on PGase I activity (Table 1). However, a substantial amounts of both PGase were lost in this process. It appears that part of the unwanted protein was removed but about 37% of PGase I and 26% of PGase II were lost to permeation through the membrane. The leak out of PGase could be due to the dissociation of PGase proteins to smaller units. Kikuchi and Sakaguchi (1973) reported that the approximately 200 kd PGases could be dissociated to 90 and 125 kd species, respectively, depending on enzyme environment. Additionally, UF was found ineffective in separating PGase I from II in their dissociated form by concentrating the higher molecular weight units of PGase II in the retentate at the expense of PGase I, exploiting the difference in MW Between the two PGases. Since the loss of both PGase I and II activities in the ultrafiltrate was substantial, the use of a membrane with MWCO of less than 100 kd may be essential to overcome this problem.

TABLE 1

Deamidation Activity and Yield of PGase after Ultrafiltration using 100 kd MWCO membrane

| Enzyme Fraction | Specific Activity (Units/mg Protein/2 hr)[a] | | |
|---|---|---|---|
| | CBZ-L-glutamine (PGase I) | BOC-L-glutaminyl-L-proline (PGase II) | Peptone Type IV (PGase I & II) |
| Crude Extract | 25.5 (100) | 18.3 (100) | 22.4 |
| Permeate | 22.5 (37) | 21.3 (26) | 20.6 |
| Retentate | 22.3 (63) | 30.6 (74) | 31.0 |

[a]Values in parentheses are percent of total PGase recovered.

TABLE 2

PGase Recovery and Extent of Deamidation upon UF Separation of Enzyme from Reaction Mixtures in Sequential Runs with 100 kd Membrane

| Run | Specific Activity (uM Ammonia/mg/2 hr)[a] | | % Peptone Deamidation |
|---|---|---|---|
| | PGase I | PGase II | |
| 1 | 21.7 (76) | 29.8 (80) | 59.0 |
| 2 | 18.3 (58) | 22.0 (60) | 57.8 |
| 3 | 16.4 (42) | 14.0 (44) | 32.0 |
| 4 | 7.4 (25) | 6.6 (26) | 25.0 |

[a]Values in parentheses are percent of total PGase recovered.

Peptone Deamidation and PGase Recovery by 100 kd Membrane

The 100 kd membrane was also used for the separation of PGase from reaction products, after the enzyme was used in the deamidation of the peptone type IV. Since the pH and the ionic strength of reaction mixtures were relatively mild, and hence unfavorable for PGase dissociation, the 100 kd membrane was used to see whether the leakout would stop by continuing UF and to study the effect of the whole process under these conditions on enzyme activity. The retentate was used 4 times to deamidate 4 batches of the peptone. Each run consisted of two steps, the first one was carried out by incubation PGase mixed with peptone at initial E/S ratio that was 1.5 times the amount sufficient for the completion of the deamidation reaction in 2 hr at 30°. The second step was a UF run that was carried out for the removal of enzyme from the deamidated peptone. An average of 24.1 and 20.6% of the total activity units of PGase I and II permeated through the membrane and were lost after each run. In addition to the leakout, there are also loss by inactivation after the 2nd run. The results in Table 2 show that after four runs the specific activity of PGase I dropped to 34% and PGase II to 22%. Based on the mechanism of UF, the loss of both enzymes, during the sequential runs was probably due to increasing destruction of enzyme by shear forces, since the MW of PGase after being dissociated was very close to the membrane MWCO. The loss in enzyme activity due to filtration and inactivation was substantial.

The total PGase units recovered at the end of each run varied from one run to another and averaged 76.2, 75.5, 72.3, and 59.2% for PGase I and 79.7, 75.3, 72.6 and 59.0% for PGase II, respectively, in the sequential runs. Therefore, starting with 100 units of PGase an average of 76, 59, 43, and 25% of the units could be recovered in the 4 runs (Table 2). The extent of peptone deamidation after each run was calculated as the ratio of the ammonia released enzymatically to either the total amides in the peptone (% deamidation) of the maximum amount if peptone amides that can be deamidated by PGase (conversion ratio). The conversion of amide groups to carboxyl groups in peptone was the maximum amount of PGase deamidation, was 1 for the first and second runs, and 0.6 and 0.5 for the third and 4th runs respectively. These levels of conversions were corresponding ti 59, 58, 32, and 25% deamidation in the peptone. Since the initial E/S ratio was sufficient to complete the peptone deamidation and the amount of peptone used in each run was dependent on the residual enzyme after sampling, the decline in conversion was due to the drop in the enzyme to substrate ratio in the 3rd and the 4th runs. UF may still be a suitable technique for recovering substantial amount of PGase enzyme after being utilized in the deamidation reaction providing the loss of protein and enzyme activity can be overcome by using a membrane with a MWCO of less than 100 kd. A membrane with a MWCO of about 3-50 kd is suitable to ensure no loss of activity as deamidation, soy protein hydrolysate is removed in the ultrafiltration.

Partial Purification of PGase by 30 kd Membrane

Table 3 presents the specific activity of PGase in the cell extract and its two UF fractions, using the 30 kd membrane. The specific activity of the starting cell extract in Table 3 was different from that of the cell extract of Table 1, probably due to preparation conditions and/or inactivation by freezing and thawing upon multiple use. UF with 30 kd membrane increased the specific activity of PGase (I and II) in retentate by 1.25 fold, with 99% activity recovery in the retentate. Also, the deamidating activity of the retentate fraction toward the peptone increased 1.25 fold. No activity was detected in the permeate fraction (Table 3). It appears that the molecular weights of dissociated products of both PGases were greater than 30 kd as no activity was lost to permeation through the membrane.

TABLE 3

Deamidation Activity and Yield of PGase after Ultrafiltration using 30 kd MWCO membrane

| Enzyme Fraction | Specific Activity (Units/mg Protein/2 hr)[a] | | |
|---|---|---|---|
| | CBZ-L-glutamine (PGase) | BOC-L-glutaminyl-L-proline (PGase II) | Peptone type IV (PGase I & II) |
| Cell Extract | 12.0 (100) | 33.9 (100) | 32.4 (100) |
| Permeate | 0.0 | 0.0 | 0.0 |
| Retentate | 14.6 (99) | 42.7 (99) | 41.6 (99) |

[a]Values in parentheses are percent of total PGase recovered.

Peptone Deamidation and PGase Recovery by 30 kd Membrane

The 30 membrane was used to filter the protein hydrolysate solution to remove species having a molecular weight greater than 30 kd in order to achieve complete separation of peptone from enzyme at the end of UF run. Permeate fraction contained 99.5% of the peptone protein. The retentate, from PGase purification by the 30 kd membrane, was used to deamidation 4 batches of the peptone. As in the 100 kd membrane runs, experiment was designed so that the first peptone batch, about 100% of the total amide groups that could be deamidation be PGase were converted to carboxyl groups, before recovering the enzyme by the UF step. The UF run was carried out for the removal of enzyme from the deamidated peptone. No. activity units of PGase I and II were permeated through the membrane or lost to inactivation after each run as evidenced by the unchanged specific activities of these two enzymes (Table 4). About 96.8% of PGase was recovered after the 4th run. This high level of recovery was due to the use of an appropriate MWCO of the membrane, which eliminated the loss of PGase activity due to leakout and concurring inactivation. In addition, the use of spiral wound membrane instead of the hollow fibers one, as well as the low pressures (10 mL/min) in these UF runs are important factors in eliminating enzyme loss by adsorption and shear forces, respectively.

TABLE 4

PGase Recovery and Extent of Deamidation Upon UF Separation of Enzyme from Reaction Mixtures in Sequential Runs with 30 kd Membrane

| Run | Specific Activity (uM Ammonia/mg/2 hr)[a] | | % Peptone Deamidation |
|---|---|---|---|
| | PGase I | PGase II | |
| 1 | 14.5 (99) | 43.0 (99) | 58.5 |
| 2 | 14.5 (99) | 42.9 (98) | 58.9 |
| 3 | 14.4 (98) | 42.4 (98) | 58.2 |
| 4 | 14.3 (97) | 42.5 (97) | 59.2 |

[a]values in parentheses are percent of total PGase recovered.

Therefore, UF with the 30 kd spiral membrane is a very suitable technique for recovering most of PGase enzyme after being utilized several times in the deamidation reaction of food proteins or protein hydrolysates having MW of less than 30 kd. Accordingly, UF can be used for the physical immobilization of PGase, although this approach does not fit the conventional conception of enzyme immobilization. Since the two most important criteria for successful UF use in enzyme immobilization, complete conversion and enzyme recovery, were satisfied here, UF is considered a suitable technique for PGase immobilization.

EXAMPLE 3

Section II: Developing Methodology for UF Reactor

Batch Ultrafiltration Reactor for Large-scale Deamidation of Food Protein by *Bacillus circulans* Peptidoglutaminase

MATERIALS AND METHODS

Preparation of PGase

*B. circulans* (ATCC 21590) cells were grown, harvested and extracted as previously described. Cell extract was ultrafiltered at 5° C. in a diafiltration mode (FIG. 1A) at 10 mL/min flux in an UF device from Amicon employing a spiral membrane with molecular weight cut-off (MWCO) of 30 kd (Amicon Corp., Lexington, Mass.). The retentate fraction in 0.02 M sodium phosphate buffer, pH 7.0 was freeze-dried and stored at −10° C. until used.

Enzyme Activity and Kinetic Constants

A 1 mL enzyme preparation containing 0.25–0.50 mg protein was added to 2–5 mL substrate in 0.05 M phosphate buffer, pH 7.0. The substrate concentrations were 0.2% CBZ-L-Gln, 0.2% BOC-Gln-Pro and 0.2% peptone type IV. Peptone solutions (5%) were ultrafiltered prior to use, through the 30 kd spiral membrane incubated at 30° C. for 30 or 60 min, then the ammonia constant of the samples was determined with a model 95-10 ammonia electrode (Orion Research Inc., Cambridge, Mass.).

The effects of the molarity and pH of the sodium phosphate buffer on PGase activity were studied. The progress of the PGase deamidation reaction of Peptone IV in 0.05 M phosphate buffer, pH 7.0, as a function of time was measured at 25° C. and 30° C. The $K_m$ and $V_{max}$ values of PGase using CBZ-glutamine, BOC-glutaminyl-proline and Peptone type IV in 0.05 M phosphate buffer, pH 7.0, were measured at 30° C. by determining the variation in the rate of PGase reaction (v) with increasing substrate concentration [S]. The 1/v was plotted against the 1/[S] to obtain a straight line (lineweaver-Burk plot) with the values of $1/k_m$ and $1/V_{max}$ taken from the intercepts with the 1/[S] and 1/v axes respectively.

Reaction Time Course

Reactions were initiated by adding 50 mL of deionized water containing 40 mg PGase to 850 mL peptone solution in 0.05 M buffer, pH 7.0, containing 15.0 g UF peptone. The reaction mixture was incubated at 30° C. and a 10 mL sample (in duplicates was taken at initial time and every 30 min for ammonia analysis. The progress of the deamidation reaction as a function of time was plotted.

Reaction Time Course in UF Recycle Mode

Figure 1B:
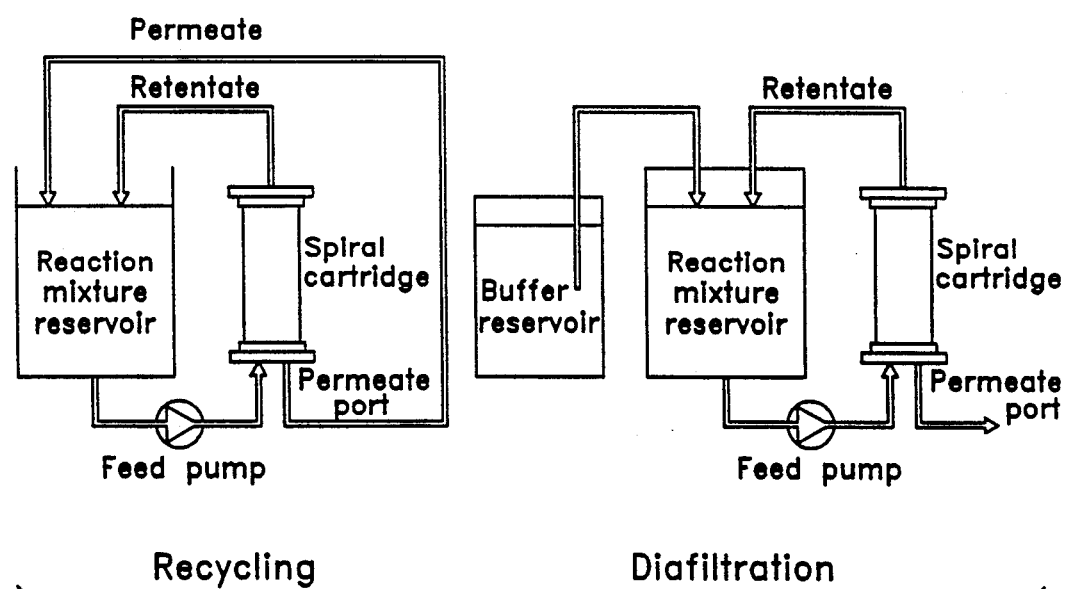

The Spiral sound S1-Y30 membrane with MWCO of 30 kd, mounted to a CH2 unit, both from Amicon Corp., was used to design a one liter reactor. About 900 mL of reaction mixture containing 15 g of UF peptone, 40 mg PGase retentate and 40 mmoles sodium phosphate buffer, pH 7.0, were ultrafiltered at 30° for 4 hr in a recycling mode (see FIG. 1B), which was a concentration mode with both the retentate and permeate recirculated back to reaction mixture reservoir, at flux rate of 10 mL/min. A 10 mL sample was taken (in duplicates) from reservoir at 0 time and every 30 min. Samples were analyzed for their contents of ammonia and the progress of the deamidation was calculated. Extent of deamidation at any point of the progress curve was expressed as conversion rate, which is defined as follows:

$$X = \frac{(S_o - S)}{S_o}$$

where $S_o$ and $S$ are substrate concentration at O time and at t time.

Since 1 g Peptone protein (Nx6.25) contained 0.67 mmoles amides and a maximum of 59% of these amide groups could be converted to carboxylic groups by PGase, releasing of 0.40 mmoles ammonia from 1 g peptone protein is equivalent to 100% conversion (X=1). The effect of UF on the reaction time course was expressed as operational effectiveness factor ($n_o$), the ratio of amide conversion at any point of the progress curve to the corresponding point in the progress curve measured outside the UF device. A Michaelis-Menten equation integrated for mixed zero and first-order kinetics (Fullbrook, 1983 and Cheetham, 1986) was modified by incorporating the effectiveness factor into it for use in calculating the amount of enzyme required to effect conversion to a certain degree or perhaps completion and in predicting the actual progress curve for given amounts of substrate and enzyme.

$$t = \frac{S_o X + K_m \cdot \ln[1/(1-X)]}{V_{max}^{no}}$$

Where t is reaction time, $S_o$ is initial substrate concentration, and X is the conversion rate.

Reaction Time Course in UF Recycle and Diafiltration Modes

The 30 kd spiral membrane reactor was operated in recycle mode for 2 hr and diafiltration mode for 2 hr (FIG. 1B), to effect the complete conversion of the peptone sample and to recover the enzyme for reuse. The starting volume of reaction mixture was 880 mL. It contained 7.7 g of peptone type IV, 25 mg PGase retentate, as calculated by the Michaelis-Menten equation, and 45 mmoles sodium phosphate buffer, pH 7.0. Recycling was carried out at 30° C. for at a flux rate of 10 mL/min. Samples (10 mL) were taken in duplicates at initial time and every 30 min for ammonia analysis. Then UF was run at 30° C. in a diafiltration mode (using 0.5 M sodium phosphate buffer, pH 7.0) with the retentate returning to reservoir and the permeate collected at 10 mL/min. A 10 mL sample was taken in duplicates from the reaction mixture and the permeate fraction every 30 min for ammonia analysis. The progress of the peptone deamidation reaction in both UF modes was determined by measuring the total ammonia released enzymatically (based on 800 mL reaction mixture containing 7.0 g peptone or 1.5 micromoles amides and 22 mg PGase) as a function of time. The operational effectiveness factor ($n_o$) was calculated as the conversion rate obtained with the UF module in recycle mode.

Maximizing Conversion

In order to maximize conversion rate by compensating the loss of activity due to UF, the amount of the enzyme was increased such that at the end of process X=1. The Michaelis-Menten equation integrated for mixed zero and first-order kinetics and UF interaction was used to calculate the amount of PGase required to complete the reaction at the end of UF process. The reaction time course was determined as described above except for the amount of enzyme used (29.1 mg) and the starting time for the diafiltration (105 min) was also calculated using this equation. The predicted reaction time course was based on 1.5 mmoles amides and 26 mg PGase. The PGase was recovered at the end of each run by the 30 kd membrane in concentration mode (FIG. 1A) at 10 mL/min flux at 5° C. The retentate was freeze dried and stored at −10° C. until used.

Parameters Affecting Enzyme Activity

The activity of an enzyme is determined by the enzyme concentration, the substrate concentration and its availability, the concentration co-factors and/or allosteric effectors, the presence, concentration and type of inhibitors, and ionic strength, pH, and temperature.

Figure 2:
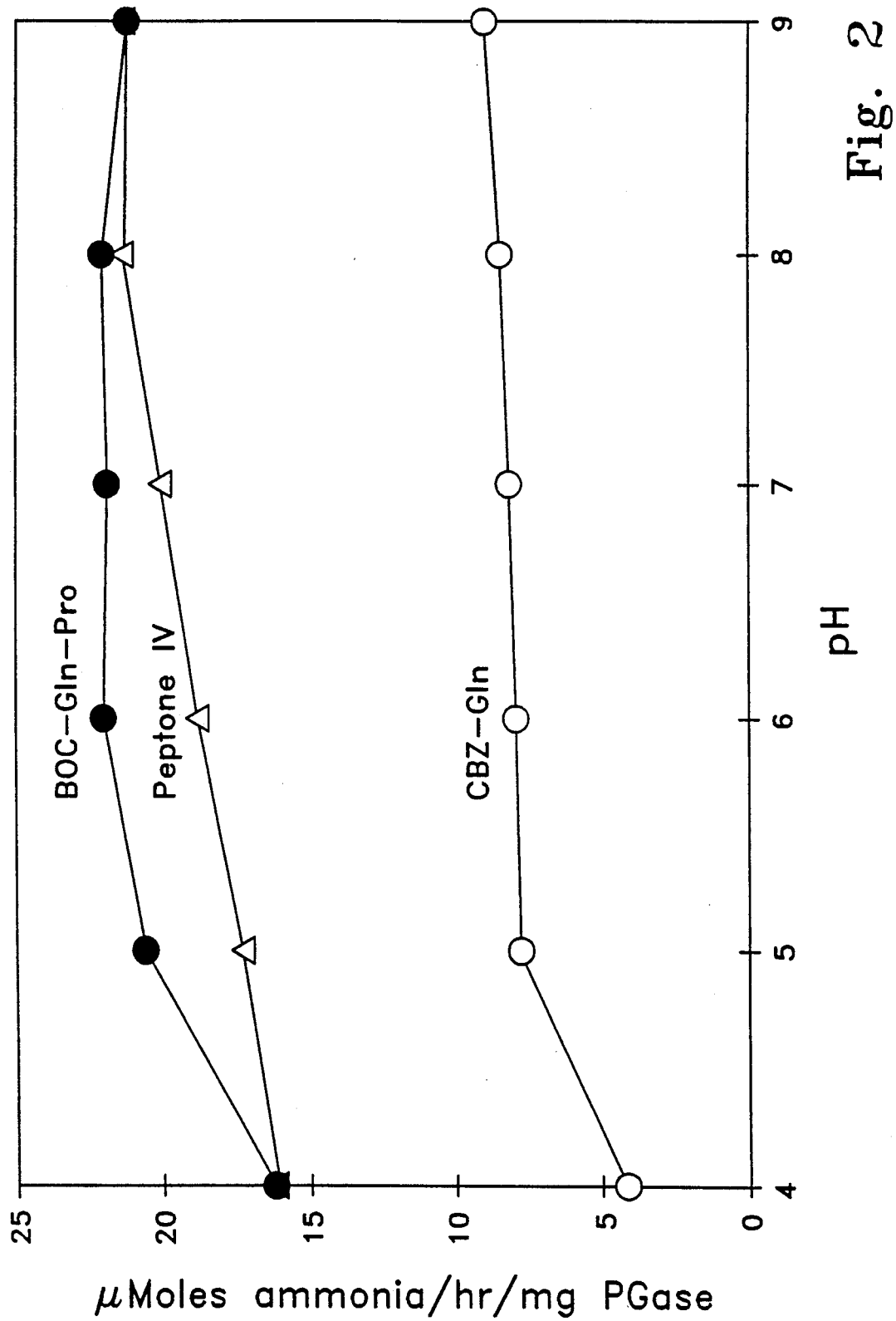
FIG. 2 Effect of pH of reaction mixture on PGase deamidation of CBZ-Gln (O), BOC-Gln-Pro (●) and Peptone IV (Δ).
Figure 3:
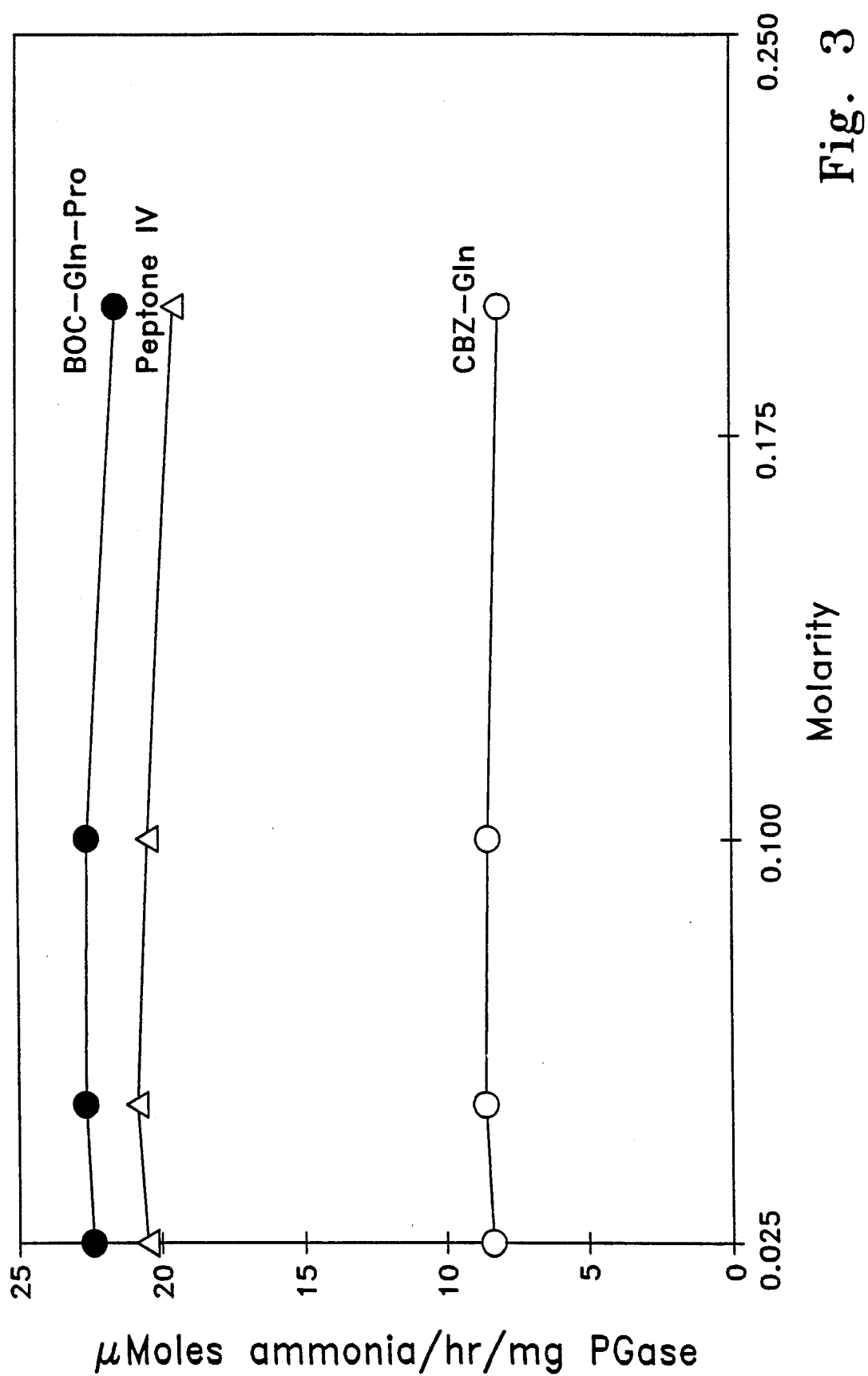
FIG. 3 Effect of buffer molarity on PGase Deamidation of CBZ-Gln (O) BOC-Gln-Pro (●), and Peptone IV (Δ).

The way in which these parameters affects enzyme activity is the study of enzyme kinetics. It gives an understanding of the reactions being studied and allows control to be exerted (Cheetham, 1986). (FIGS. 2 and 3 illustrated the effect of pH in 0.05 M phosphate buffer) and molarity of phosphate buffer at pH 7.0 on the specific activity of the PGases. These ionic strength and pH ranges were chosen for this study because the PGases, like most enzymes, are relatively stable in these mild environment (Kikuchi and Sakaguchi, 1973). Activity was virtually the same at pH range of 6–9 but dropped slightly at pH 5. The specific activity of the PGases was basically unchanged in the molarity range of 0.025 to 0.100 at pH 7.0. Data here are in complete agreement with the original findings of Kikucki and Sakaguchi (1973) as they reported that optimum pH of PGase I in Tris-HCl buffer was about 8.0 and PGase II had a broad pH profile of relatively high activity, approximately 5–11, with optimum at 8.0. When soy peptone was used as the substrate, this picture remained basically unchanged as the optimal pH range was 5–9 (FIG. 2) and optimal molarity was 0.025–0.100 (FIG. 3).

Figure 4:
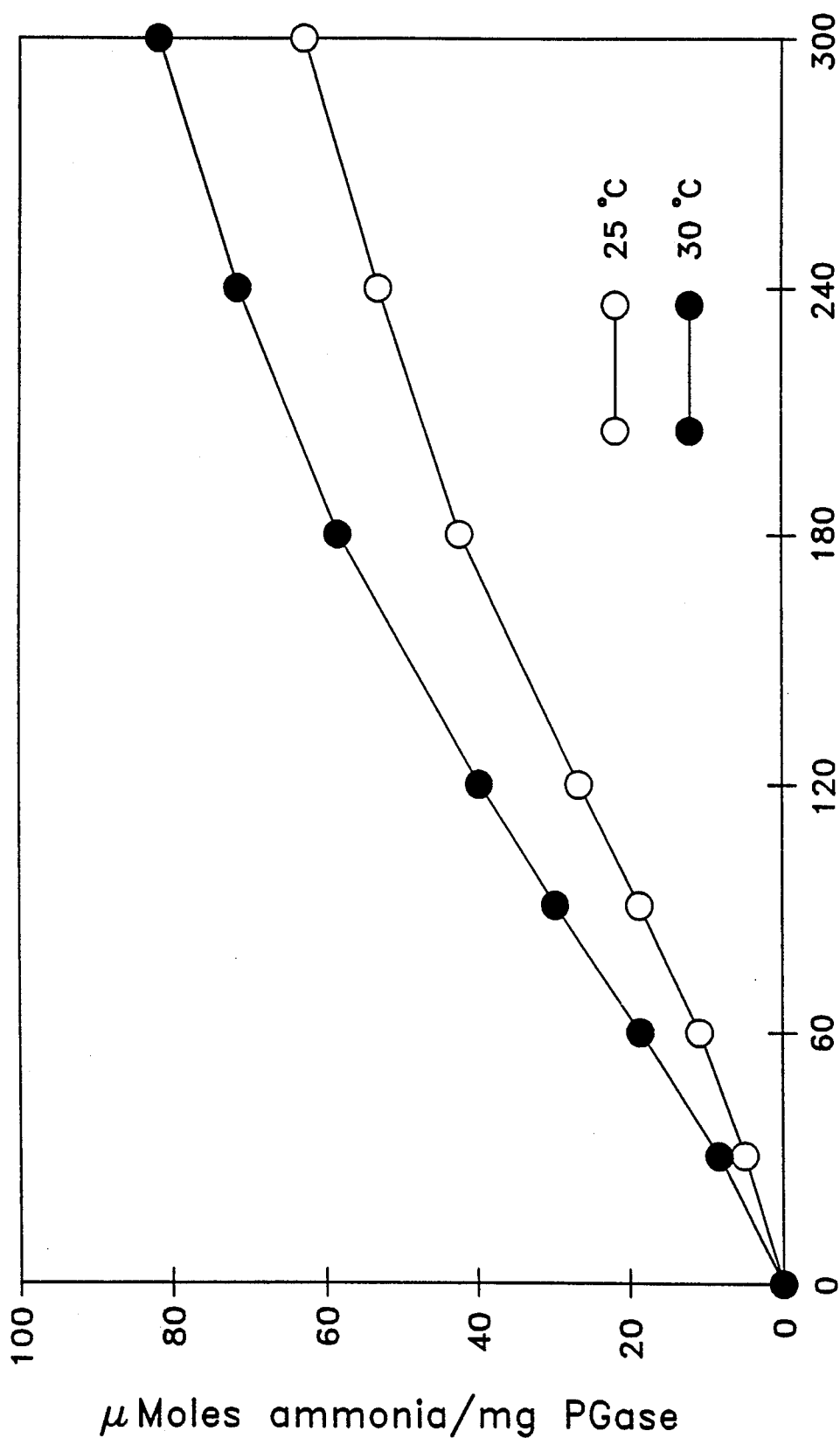
FIG. 4 Effect of reaction temperature of PGase deamidation of Peptone IV: (O) 25° C.; (●) 30° C.

As would be expected peptone deamidation progressed faster at 30° C. than at 25° C. (FIG. 4) Since activity of PGase, and hence the progress of peptone deamidation, tend to vary depending on the composition and condition of reaction mixture, these parameters were kept constant in initial velocity determinations used in designing an UF reactor.

Initial Velocities and Prediction of Reaction Time Course

The quantification and prediction of the performance of a physically immobilized enzyme in a reactor as compared to the initial velocity experiments can be achieved by using mathematic models of batch reactors driven from the Michaelis-Menten equation (Cheetham, 1986). The linewaver-Burk plot gave $K_m$ values of 0.67, 1.43 and $1.67 \times 10^{-4}$ M and $V_{max}$ values of 0.08, 0.52 and 0.48 micromoles/min/mg for CBZ-glutamine, BOC-glutaminyl-proline and Peptone type IV, respectively (Table 5). As previously mentioned and as indicated in (FIGS. 2 and 3), the PGase activity toward the Peptone type IV was apparently correlated to PGase II activity but not PGase I activity. This observation is confirmed here by the almost identical $K_m$ and $V_{max}$ values for BOC-glutaminyl-proline and Peptone type IV substrates.

Accordingly, the PGase Kinetics for other food proteins or protein hydrolysates when used as substrates can be integrated using the data of Peptone type IV, instead of that of BOC-glutamine-proline, since the latter substrates is relatively far more expensive.

TABLE 5

$K_m$ and $V_{max}$ Values for Peptidoglutamine Substrates

| Subtrate | $K_m$ (M × 10$^{-4}$) | $V_{max}$ (micromoles/ min/mg) |
|---|---|---|
| CBZ-glutamine | 0.67 | 0.88 |
| BOC-glutamine-proline | 1.43 | 0.52 |
| Peptone Type IV | 1.67 | 0.48 |

The Michaelis-Menten equation for zero-order reactions (eg.1) and the integration form of the equation for mixed zero and first-order reactions (eg.2) were used to predict the time course of PGase deamidation of Peptone.

$$V = \frac{V_{max}[S]}{[S] + K_m}$$

Where v is the initial rate of enzyme catalyzed reaction and [S] is substrate concentration.

$$t = \frac{S_o X + K_m \ln[1/(1-X)]}{V_{max}}$$

Where t is time of reaction; $S_o$ is the initial substrate concentration and X is conversion rate. The constants in Table 1 were used to solve the two equations. The value of $V_{max}$ was calculated from the specific activity of the PGase used to catalyze the Peptone IV deamidation reaction.

Figure 5:
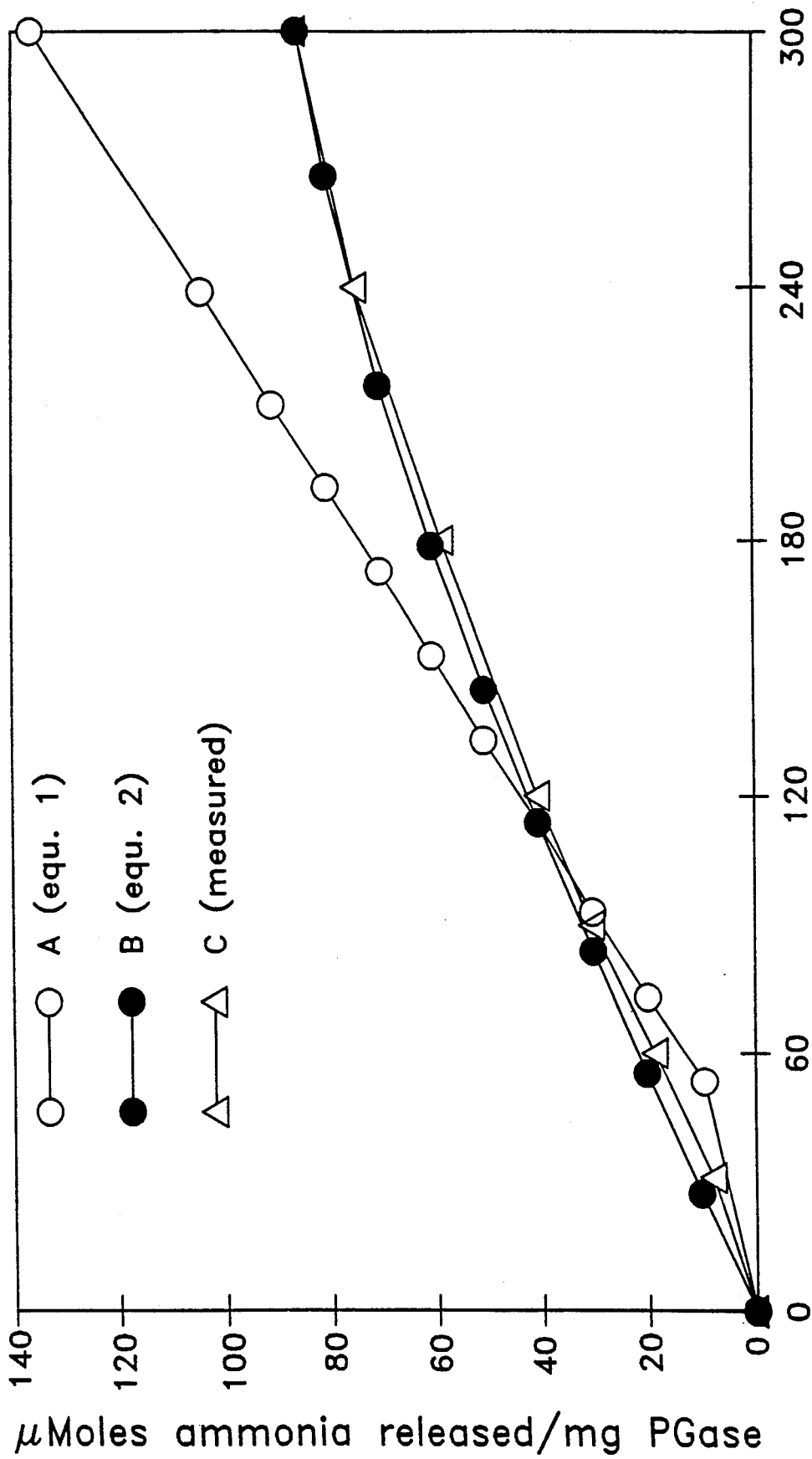
FIG. 5 Progress of Peptone IV deamidation of PGase.

A comparison of the reaction progress (time course) measured experimentally with that calculated using both equation is given in FIG. 5. As would be expected the use of eg. 1 in calculating the progress of reaction yeiled a straight line that was far removed from the experimental progress curve in its second half, which seems to be principally a first-order rate. The reason for that is the reaction velocity in the Michaelis-Menten equation is the velocity of the enzyme catalyzed reaction when the concentration of products tends to zero. But in a progress curve of a typical industrial reaction that proceeds for long periods of time, the initial reaction velocity decreases as the reaction proceeds (Fullbrook, Practical Applied Kinetics, in *Ind. Enzymol.*; Eds. Godferey, T. & Reichelt, J.; MacMillan 8-40; 1983). Because of the lowering of the average substrate concentration during such reactions, first, or mixed first and zero-order kinetics, rather than zero-order Michaelis-Menten kinetics are applied such that the rate of reaction depends directly on the prevailing substrate concentration. As indicated in FIG. 5, data of eg. 2 used to predict the time course of reaction closely matched that measured experimentally. Therefore, data obtained by eg. 2, accurately demonstrate the time course of the reaction. This equation is of particular advantage in providing the basis for modeling and optimizing configuration of reaction and to determine the best operating conditions to maximize productivity and achieve complete amide hydrolysis. In an industrial batch reaction, it is of particular interest to run an enzymatic reaction to near completion in order to maximize yield, this requires knowing the enzyme concentration and the reaction time necessary to effect a desired conversion yield (Cheetham, 1986).

Kinetics of UF Reaction in Recycle Mode

To design an UF reactor, the module was first run in a recycle or non-fractionation mode, in which both the retentate and permeate returned to the reaction mixture reservoir throughout the course of reaction FIG. 6 gives the progress of peptone deamidation by PGase as a function of time at 30° C. at 10 mL/min flux. The progress of this reaction was influenced by recycling reaction mixture as activity increased with recycling. This increase in activity could be due to the better mixing of reactant and enzyme. The effectiveness factor ($n_o$), suggested by Chambers et al. (1976) and Cheetham (1986), was calculated by equation the reaction rate at 10 mL/min flow to the reaction rate at 0 mL/min flow, i.e. with no ultrafiltration. The $n_o$ averaged 1.04 for the first half of the reaction and 1.15 for the second half. The interaction of enzyme kinetics and effect of UF can be described by equation 2 but with the inclusion of the operational effectiveness factor ($n_o$). The time, in minutes, or the overall reaction rate (micromoles/min) can then be calculated from the following equation:

$$t = V\{S_o X + K_m \ln[1/(1-X)]\}/V_{max} Q n_o$$

Where V is the total volume of reaction mixture (mL) including the fluid in any circulation tube or the membrane itself. So is the initial substrate concentration (micromoles/mL), and the $K_m$ and $V_{max}$ constants are expressed in micromoles/L and micromoles/min/mL, respectively.

Therefore $n_o$ in the equation takes into account the increase in amide hydrolysis caused by the mild circulation of reaction mixture, and must be used in predicting the time course of the reaction for a given substrate quantity and calculating the required dosage of enzyme to effect a given degree of deamidation of a given substrate quantity in a finite time.

Kinetics of UF Reactor in Recycle and Diafiltration Modes

It was deamidation that by using peptone concentration of less than 1.0%, more than 99% of the protein in 800 mL peptone solution was permeated in 2 hr UF in diafiltration mode at 10 m/Lmin. Therefore only 7 g of the peptone could be used in this size reactor of one liter capacity containing 800 mL peptone solution to insure completion recovery of products from reaction mixture. In this reactor, UF device was first operated in recycling mode, which was achieved by circulating the reaction mixture through the 30 kd membrane at a flux rate of 10 mL/min at 30° C. for 2 hr. The remainder of UF progress was run in diafiltration mode where the reaction mixture was fractionated by the membrane to retentate and permeate at 30° C. for 2 hr at flux rate of 10 mL/min. The purpose of this UF process was to recover the enzyme for reuse and also to complete the reaction to the desired degree of conversion (X), which was targeted here to be 1.00. Equation 3 was used to calculated the amount of enzyme required to complete the deamidation of the peptone in a finite time. In equation 3 the term $V_{max} = EK_2$ is the product of the enzyme present and its activity (v).

Thus the $E_o$ quantity (in mg) required to achieve a given conversion rate was calculated by substituting the term $EK_2$ for $V_{max}$. That is $$E_o = V\{S_o X + K_m \ln[1/(1-X)]\}/t\, n_o \quad (4)$$

Where EO is the enzyme concentration (mg) present at zero time. The peptone substrate contained 1.5 mmoles amide groups, which required, 22 mg PGase to attain complete conversion in 4 hr under the conditions described above including that the UF unit being in recycle mode. Equation 3 was also used to calculate the progress of reaction for the amounts of amides and enzyme in the reactor, using $n_o = 1.2$. That is $$t = V\{S_o X + k_m \ln[1/(1-X)]\}/V_{max}\, n_o \quad (5)$$

FIG. 7 (A) shows the predicted time course of reaction for 1.5 mmoles amides and 22 mg PGase. Since enzyme should be recovered by switching from recycle mode to fractionation mode, and at least 2 hr was needed to completely separate the enzyme from products, a cut-off time for the switch was 2 hr. At the cut-off time conversion was 0.6 (FIG. 7A). The experimental progress curve of this reaction, with module in two modes, as a function of time is shown in FIG. 7B. As in recycling mode, the maximum rate of reaction occurred very soon after starting the reactor.

The catalytic efficiency of the enzyme continued basically at the same rate until nearly half of the substrate converted to product then decreased subsequently during the course of the reactor. However, the reaction rate in the second half of this progress curve (B in FIG. 7) was 85% less than that of recycle mode reaction (A in FIG. 7). At the end of this batch run a conversion rate of only 0.85 was obtained. This was not surprising since operating in a fractionation mode which included permeation should have some reduction effect on the rate of deamidation. On the other hand, one would expect that increasing the E/S ratio by the continuous removal of substrate or product by UF would increase the conversion rate. There could be also immobilization effect, i.e. the substrate must pass by the enzyme before permeation. Contrary to the permeation effect, these effects would result in a higher conversion ratio. Therefore the performance of immobilized PGase must be determined by the interaction of the enzyme kinetics with such UF effects as suggested by Chambers et al. (1976) and Cheetham (1986). For this particular system, the interaction of PGase kinetics and UF and permeation effects can be easily described using e.g. The effectiveness factor ($n_o'$) is the ratio of the reaction rate in diafiltration mode, to the reaction rate in a non-fractionation recycle mode. Thus $n_o'$ takes into account the change in substrate metabolism caused by both the presence of the membrane and the effect of permeation. The $n_o'$ value in the last 2 hr of UF process while module in difiltration mode, averaged 0.85, which indicated reduction in substrate turnover (compare 7A with 7B) due to the UF fractionation process.

Operational Effectiveness Factors and Maximization Deamidation

In industrial reactors the complete reaction of concentrated substrate solutions are often wanted, which may require increasing enzyme dosage and/or for the reaction to occur continuously for long time periods (Fullbrook, 1983). Therefore the rate of reaction is controlled by the amount of enzyme present such that the time required to achieve the targeted product concentration can be controlled by the concentration of enzyme present. Accordingly, larger concentrations of enzyme were needed to maintain rate of reaction, so that completely converted substrates (i.e. X=1.00) could be obtained at the end of UF run. The enzyme concentration was calculated using eg. 6 that was driven from eg. 5, which takes into account the reduction in deamidation rate caused by UF when calculation was based on the effectiveness factor of $n_o'=0.85$.

$$E_o = V\{S_oX - K_m \ln[1/(1-X)]\} t \; n_o n_o' \qquad (6)$$

It was found that 26 mg PGase were required to complete deamidation at the end of UF run. As with the above experiment UF, diafiltration sated when X=0.6, which was the time for switching from recycle to diafiltration mode and was determined by equation 5 and found to be min. Equation 5 then can be written as follows: $t = 800 \; (0.6X + 0.92 \; K_m/V_{max} \; n_o$. Since the product of $n_o n_o' = 1.00$, equation 3 and 4 can replace eg. 5 and 6 in calculations using the same experimental applications since the rate of reaction is usually controlled by varying the enzyme concentration used an/or the period of reaction in order to achieve the desired degree of conversion at a fixed rate of reaction.

The reaction rate using 26 mg PGase was slightly higher than that using 2 mg PGase (FIG. 7B and C).

The maximum conversion was about 0.96 at the end of the process. Therefore in order to maximize the deamidation process, it is imperative to use slightly higher concentration than that calculated. Fullbrook (1983) stressed that the enzyme dosage calculated by this Michaelis-Menten expression should be regard as the minimal level required, since it is unlikely that the enzyme will maintain its full activity during the whole course of the reaction.

Pretreatment of Protein Substrate

Since the MWCO of the spiral membrane is 30 kd, protein substrate with higher molecular weight must be hydrolyzed by a suitable protease prior to application to the bioreactor Heat treatment, prior to or post proteolysis, is required in order to increase the substrate susceptability to PGase attack. Prefiltration employing a 50-100 micron membrane is essential to remove coarse insolubles that might foul (plug up) the membrane. Use of a 30 kd membrane to produce protein species having molecular weigh of less than 30 kd and to improve reactor performance is also necessary pretreatment of protein substrate.

The present invention has the advantage of providing a membrane bioreactor in which the enzyme responsible for deamidation remains separate from the food product and can be re-used a number of times, thus increasing productivity of the system. Use of the spiral membrane bioreactor additionally offer high product recovery because of the low adsorption of the membrane.

It can be seen, there has been provided in accordance with the present invention methods for the large-scale deamidation of proteins using ultra-filtration. The invention as described by the specific embodiments is not meant to limit its scope. It is envisioned and apparent what many alternatives and variations may be emcompassed by the present invention. It is intended that the spirit and scope of this disclosure include such alternatives and variations.

I claim:

1. A process for enhancing solubility and functional properties of soy proteins which prevents enzyme contamination of the deamidated protein product and maximizes enzyme recycling comprising:
    a) hydrolyzing the soy protein with a suitable protease should its molecular weight exceed the molecular weight cut-off used in the semipermeable membrane of step c),
    b) solubilizing soy protein to provide a solubilized protein having a predetermined molecular weight,
    c) providing a reactor vessel divided by a semipermeable membrane into a feed portion and a permeate portion and, an enzyme present in the feed which will deamidate said solubilized protein, wherein said semipermeable membrane has a molecular weight cut-off smaller than the molecular weight of the enzyme and larger than the molecular weight of the solubilized protein,
    d) adding the solubilized protein to the feed portion of the reactor vessel to provide a reaction mixture which is allowed a time and temperature sufficient to deamidate said solubilized protein, and
    e) allowing said demodulated protein to permeate said semipermeable membrane;
wherein said soy protein is heat treated prior to inclusion in the reactor vessel.

2. The method in claim 1, wherein the solubilizing step a) is accomplished by any one of the methods selected from the group consisting of solvent extraction heat denaturization and extraction, proteolysis, and detergent solubilization.

3. The method of claim 1, wherein the enzyme capable of deamidating said solubilized protein is selected from the group consisting of proteases, peptidoglutaminases and transflutaminases.

4. The method of claim 3, wherein the semipermeable membrane is one which either minimizes or eliminates concentration polarization.

5. The method of claim 3, wherein the semipermeable membrane is a spiral membrane.

6. The method of claim 5, wherein the reactor vessel is a continuous flow reactor or a batch reactor.

7. The method of claim 5, wherein the semipermeable membrane has a molecular weight cut-off of from about 3 to about 50 kd.

8. The method of claim 1, wherein the enzyme is bound to a solid support.

9. The method of claim 8, wherein the enzyme is bound to the semipermeable membrane.

* * * * *

UNITED STATES PATENT AND TRADEMARK OFFICE
CERTIFICATE OF CORRECTION

PATENT NO. : 5,250,305
DATED : Oct. 5, 1993
INVENTOR(S) : Jamel S. Hamada

Page 1 of 2

It is certified that error appears in the above-indentified patent and that said Letters Patent is hereby corrected as shown below:

On the Title page, in the Abstract, line 2; change "foot" to -- food --.

Column 1: line 14, change "foot" to -- food --; line 18, change "foot" to -- food --; line 28, change "enchance" to -- enhance --; line 32, change "aproach" to -- approach --; line 33, change "serval" to -- several --; line 42, change "todeamidation" to -- to deamidate --; line 44, change "deamidation soypeptides" to -- deamidate soy peptides --; line 45, change "intaaaact" to -- intact --; line 60, change "coinventional" to -- conventional --; line 61, delete "a".

Column 2: line 24, change "consitions" to -- conditions --; line 36, change "alternation" to -- alteration --; line 59, change "therefor and" to -- therefore an --; line 64, change "e.s." to -- e.g. --.

Column 3: line 1, change "lose" to -- loss --.

Column 5: line 43, change "ph" to -- pH --; line 54, change "Do." to -- Co. --.

Column 8: line 8, change "ti" to -- to --; line 56, before "membrane" insert -- kd --; lines 65 and 66, change "deamidation be" to -- deamidated by --.

Column 9: line 1, change "No." to -- No --.

Column 10: line 24, change "(in duplicates" to -- (in duplicates) --; line 39, change "A$_{10}$" to -- A 10 --.

UNITED STATES PATENT AND TRADEMARK OFFICE
CERTIFICATE OF CORRECTION

PATENT NO. : 5,250,305
DATED : Oct. 5, 1993
INVENTOR(S) : Jamel S. Hamada

It is certified that error appears in the above-indentified patent and that said Letters Patent is hereby corrected as shown below:

Column 12: line 58, change "(eg.1)" to -- (eq. 1) --; line 59, change "(eg.2)" to -- (eq. 2) --; line 64, after the formula insert -- (eq. 1) --.

Column 13: line 2, after the formula insert -- (eq. 2) --; line 14, change "eg. 1" to -- eq. 1 --.

Column 14: line 1, after the formula insert -- (eq. 3) --; line 19, change "deamidation" to -- determined --; line 45, after the formula insert -- (eq. 4) --; line 56, after the formula insert -- (eq. 5) --.

Column 15: line 23, change "e.g." to -- eq. 6 --; line 48, change "eg." to -- eq. --; line 49, change "eg." to -- eq. --; line 53, after the formula insert -- (eq. 6) --; line 61, change "eg." to eqs. --; line 68, change " 2 mg" to -- 22 mg --.

Claim 3: line 4, change "transflutaminases" to -- transglutaminases --.

Signed and Sealed this

Twenty-sixth Day of July, 1994

Attest:

BRUCE LEHMAN

*Attesting Officer*  *Commissioner of Patents and Trademarks*